United States Patent [19]

Kramer et al.

[11] Patent Number: 4,810,810

[45] Date of Patent: Mar. 7, 1989

[54] NEW ORGANO-ALUMINUM ANTIPERSPIRANT COMPOSITIONS

[75] Inventors: Hildegard M. Kramer, Westport; Lewis S. Meriwether, Wilton, both of Conn.

[73] Assignee: American Cyanamid Company, Stamford, Conn.

[21] Appl. No.: 762,085

[22] Filed: Aug. 2, 1985

[51] Int. Cl.$^4$ .............................................. C07F 5/06
[52] U.S. Cl. .................................. 556/175; 556/182
[58] Field of Search .............................. 556/175, 182

[56] References Cited

U.S. PATENT DOCUMENTS

| | | | |
|---|---|---|---|
| 2,801,190 | 7/1957 | Orthner et al. | 556/182 X |
| 2,823,169 | 2/1958 | Brown et al. | 556/182 |
| 3,256,188 | 6/1966 | Papayannopoulos | 556/182 X |
| 3,420,932 | 1/1969 | Jones et al. | 556/182 X |
| 3,444,226 | 5/1969 | Schmank et al. | 556/175 |
| 3,444,292 | 5/1969 | Beekman et al. | 556/175 X |
| 3,446,585 | 5/1969 | Tanabe | 556/175 |
| 3,472,929 | 10/1969 | Jones et al. | 556/182 X |
| 3,734,940 | 5/1973 | Rubino et al. | 556/175 |
| 3,792,070 | 2/1974 | Jones et al. | 556/175 |
| 3,819,671 | 6/1974 | Bouillon et al. | 556/175 |
| 3,956,352 | 5/1976 | Bouillon et al. | 556/175 |
| 4,447,364 | 5/1984 | Staal | 556/175 |

*Primary Examiner*—Paul F. Shaver
*Attorney, Agent, or Firm*—C. J. Fickey

[57] ABSTRACT

A method for producing heterocyclic aluminum compounds of the formula:

$$[(C_3H_8O_2)_x (Al)_y (Cl)_z]_n$$

where X=1, Y=1, Z=1-2, and n=1-20, by reacting aluminum chloride with a short chain alkanol or polyol in the presence of an inert solvent, and the composition obtained in the reaction which is useful as an anti-perspirant compound.

4 Claims, No Drawings

NEW ORGANO-ALUMINUM ANTIPERSPIRANT COMPOSITIONS

The present invention relates to organic aluminum compounds and to methods for their preparation. The compounds of the present invention are particularly useful for anti-perspirants. Because of their solubility in absolute alcohol, and their compatibility with fluorocarbon propellants, they are readily adaptable for use in aerosol formulations or other forms of antiperspirants.

The requirements for successful dispensing of antiperspirant compositions by aerosol are quite rigorous. The anti-perspirant compositions must form clear, homogeneous systems with anhydrous (95 to 100%) ethanol and fluorocarbon propellants. They must not precipitate or gel within reasonable storage periods. They should contain only trace amounts of iron, since this metal inactivates compounds such as "hexachlorophene" and also catalyzes degradation of some organic perfume materials. The anti-perspirant compositions should have a low acidity pH range on the order of 3.5 to 4.5 when mixed with water. They must be sufficiently soluble to be effective and they must be safe to use daily on the skin. Most important, they must be effective in inhibiting the flow of perspiration on the axillae.

Aluminum chloride hexahydrate has been used as an anti-perspirant composition for a long period of time. Although it is compatible with anhydrous ethanol, and compatible with propellants, and as an effective anhydrotic it is too acid to use daily, and has adversely affected the tensile strength of fabrics. Less acid materials such as aluminum phenolsulphonate has been used as an anti-perspirant composition, but the anti-perspirant activity of this materials is quite low. The patent literature also includes a disclosure of aluminum chlorhydroxide alcoholate haveing 0.25 to 1 hydroxyl for each aluminum atom in anti-perspirant compositions (U.S. Pat. No. 2,823,169). These materials, however, are rather unstable and they contain more than a trace amount of iron, usually including on the order of 40 to 80 parts per million of iron. U.S. Pat. No. 2,872,379 discloses a series of alkoxy aluminum chlorides as anti-perspirants, but these compounds are limited in the usefulness because of their very low solubility in anhydrous alcohol.

One of the objects of the present invention is to provide an improved series of aluminum containing antiperspirant materials which are readily soluble in ethanol of 95 to 100% concentration, and which are compatible with conventional fluorocarbon propellants.

Another object of the invention is to provide a series of anti-perspirant compositions in which the aluminum atom is part of a heterocyclic ring including oxygen and carbon atoms, and being not unduly acidic.

A further object of the invention is to provide a series of heterocyclic aluminum compounds which may be used in solid antiperspirant sticks and fluid roll-on formulations.

The organic aluminum compounds of the present invention have the general formula:

$$[(C_3H_8O_2)_x(Al)_y(Cl)_2]_n$$

where $X=1$, $Y=1$, $Z=1$ to 2 and $n=1$ to 20. The inventive compounds are formed by reacting aluminum chloride with a short chain alkanol or polyol of from 2 to 6 carbon atoms in the presence of an inert solvent. The reactive alkanol may be substituted by hydroxy groups on carbon atoms which are spaced apart by no more than one carbon atom. Suitable reactive alkanols are, for example ethylene glycol, hexylene glycol, 1, 3 propylene glycol, 1, 2-propylene glycol, 1, 2-dihydroxy cyclohexane, glycerin, ethanol, propanol isopropanol, hexanol and the like.

Suitable inert solvents are those which are inert to both aluminum chloride and the reactive alkanol and in which both reactants are soluble, for example, ethyl ether, tetrahydrofuran, dioxane, diglyne, diethylether, methylene chloride, chloroform and the like.

The ratio of reactants is generally 1:1 or excess alkanol may be used.

The following specific examples illustrate preparation of the organo-aluminum complexes by the process of the present invention, and the efficaceousness of these compounds as antiperspirant compounds.

EXAMPLE I

Preparation of AlCl$_2$ (propyleneglycol).H$_2$O Complex

A 250 ml reaction vessel equipped with magnetic stirring bar, condenser, drying tube and addition funnel was charged with 25 g (0.19 mole) of AlCl$_3$ (anhydrous). The AlCl$_3$ was weighed and transferred in a glove bag under nitrogen. External cooling using ice-acetone was applied to the reaction vessel and 250 ml diethylether was added dropwise with stirring at 0°–5° C.

Propyleneglycol 15.4 g (0.19 mole) was dissolved in 50 ml of diethylether and added dropwise to the AlCl$_3$-ether solution over a period of 20 minutes. Good stirring was maintained throughout the addition. A white precipitate was formed immediately. The ice bath was removed and the reaction was allowed to stir at room temperature for 5 additional hours. The product was filtered over a coarse sintered glass funnel and washed four times with 4×300 ml of ether, resuspending the solid after each washing while avoiding excessive air intake. The solid was then dried under vacuum overnight at 25° C. The solid was resuspended in 300 ml of diethylether for 30 minutes and filtered followed by a 300 ml ether rinse and drying under vacuum at 25° C. The white solid was hygroscopic and soluble in ethanol and water.

IR analysis indicates a possible structure of:

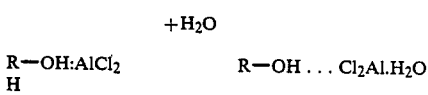

in which the complex dissociates in H$_2$O but reforms on drying. Elemental analysis gives an Al:Cl ratio of 1:2. pH readings of the complex in H$_2$O were taken. At 10% concentration the pH=3.7 and at 20% concentration the pH=3.1, compared to 10% AlCl$_3$.6H$_2$O solution with a pH of 2.7.

EXAMPLE II

Three different propyleneglycol.aluminumchloride complex preparations were tested for axillary antiperspirant activity on a panel of 20 and compared to aluminumchlorohydrate (ACH) as follows:

| Complex Run # | Sweat Reduction (%) | Sweat Reduction by ACH |
|---|---|---|
| 1 | 42.2 | 26.0 |
| 2 | 63.1 | 38.3 |
| 3 | 56.2 | 40.4 |

EXAMPLE III

Reaction of $AlCl_3$ with Isopropanol 8 g $AlCl_3$ (anhydrous) protected from air, was cooled in an ice bath. With stirring, 20 ml of isopropanol was added; continued cooling was necessary. A brownish mass was obtained with some undissolved $AlCl_3$ remaining. Additional isopropanol was added (20 ml) with stirring. A dark brown liquid was obtained. On dilution with ether a precipitate formed. The total volume of ether-alcohol was approximately 600 ml and was left over night.

The filtered off precipitate was washed thoroughly with ether to remove the brown mother liquor. A slightly colored product was obtained: Total=3.6 g.

| Assumed structure: |
|---|
| % Al found = 18.29, 18.17 |
| % ACl found = 22.4, 22.3 |

EXAMPLE IV

Reaction of $ALCl_3$ with Ethanol 9 g of $ALCl_3$ anhydrous (weighed under $N_2$ in a plastic bag) was cooled in an ice bath prior to the dropwise addition of 28 ml of ethanol. A white, oily product was obtained. 45 ml of diethylether was added to the reaction mixture and white solid precipitated out. The product was kept at 4° C. (refrigerated) over night.

The solid was filtered off, dried under vacuum.

| Total of Product = 17.6 g | | |
|---|---|---|
| Assumed structure: $ALCl_2(OC_2H5).2ALCl_3.10C_2H_5OH$ | | |
| % AL found = | 8.18, 8.25 | estimated Al = 9.3 |
| % AlCl | 32.0, 32.4 | Cl = 32.6 |

EXAMPLE V

Preparation of Hexylaluminum dichloride 0.4 moles (20.4 g) Hexylalcohol
0.4 moles (26.7 g) $ALCl_3$ andrydrous.

The $ALCl_3$ was dissolved in 60 ml of ether (avoiding moisture) and the hexylalcohol was added dropwise with stirring over a period of 30 minutes. After the addition, the reaction mixture was refluxed over night (approximately 19 hrs.)

Removed the ether on the rotary evaporator and the oily residue was added dropwise to acetone. The white parcipitant was collected by centrifugation and decanting the supernatant liquid, after redissolving the precipitate in $H_2O$, and extraction with ether was carried out to remove all unreacted hexylalcohol and $AlCl_3$. The aqueous solution was then placed on a rotary evaporator and the obtained solid dried under vacuum. The dried solid was ground to a fine powder, extracted with ether once (washed) and dried under vacuum at 60° C.

| % Al found | = | 13.45 | % calculated 13.55 |
|---|---|---|---|
| % Cl | = | 36.20 | 35.60 |

Y=Lost substantial amount of product during work-up; amount available: 8.3 g, pH (10% solution)=3.2.

EXAMPLE VI

Preparation from Lactic Acid and ALCl

A molar ratio of 1:2 Aluminumchloride:Lactic Acid $2CH_3CHCOOH +$

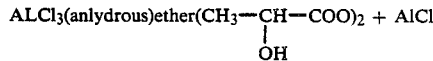

$ALCl_3$(anlydrous)ether$(CH_3-\underset{\underset{OH}{|}}{CH}-COO)_2 + AlCl$ 18.0 g(0.1 moles):6.63 g(0.05 moles). MW = 240.58

Both components were dissolved in ether in a round flask equipped with condenser and addition funnel. The lactic acid was added dropwise over a period of 60 minutes, and then refluxed for 18 minutes.

The white percipitant formed instantaneously after the addition of the lactic acid was filtered and stirred six times with 100 ml of ether for 2 to 3 hours each time to remove all unreacted testing material.

| Total product = 7.9 g | | 32.9% Field |
|---|---|---|
| Analysis: | % AL 9.87, 10.11 | % estimated 11.12 |
| | % Cl = 11.6, 11.6 | 14.60 |
| Est. | C = 29.95% | Found = C 23.85, 23.96 |
| | H = 4.52 | H = 5.82, 5.57 |

EXAMPLE VII

Preparation of Hexadecylaluminum dichloride 0.1 mole $ALCl_3$ (13.6 g) was dissolved in 30 ml of ether with cooling to avoid exotherm.

24.3 g of hxadecylalcohol (0.1 mole) was dissolved in $CH_2Cl_2$. The $ALCl_3$ solution was added dropwise to the hexadeyclalcohol with stirring. After the addition, heated the reaction mixture to reflux for approximately 19 hours.

Removed all solvent on the rotary evaporator and precipated the product in acetone. The fine solid was isolated by centrifugation. The wet solid was dissolved in water and extracted three times with 100 ml of ether to remove unreacted testing material. The $H_2O$ was removed on the rotary evaporator and the obtained solid dried under vacuum at 60° C.

| Total product = 8.7 g (estimated 33.9 g) | % Field = 25.7 |
|---|---|
| Analysis: % AL = 20.75 | (calculated, 7.95) |
| % Cl = 29.05, 28.7, 20.8 | (calculated, 20.90) |

We claim:

1. A method for producing an organic aluminum compound of the formula:

$[(C_3H_8O_2)x(Al)y(Cl)z]_n$ 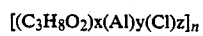

where x=1, y=1, z=1 to 2 and n=1 to 20, which comprises reacting aluminum chloride with an alkanol or polyol having from 2 to 6 carbon atoms and having hydroxyl groups on carbon atoms which are spaced apart by no more than one intervening carbon atom, in the presence of an inert solvent.

2. The method of claim 1 wherein said inert solvent is diethyl ether.

3. The method of claim 1 wherein said alkanol is propylene glycol, isopropanol, ethanol and hexanol.

4. An organic aluminum complex of the formula:

$$[(C_3H_8O_2)x(Al)y(Cl)z]_n$$

wherein $x=1$, $y=1$, $z=1$ to 2 and $n=1$ to 20, as produced by the method of claim 1.

* * * * *